/

US007025957B2

(12) United States Patent
Arquette (10) Patent No.: US 7,025,957 B2
(45) Date of Patent: Apr. 11, 2006

(54) COMPOSITION AND METHOD TO WHITEN SKIN (75) Inventor: James Demetrios G. Arquette, Tempe, AZ (US)

(73) Assignee: Desert Whale Jojoba Company, Tucson, AZ (US)

(*) Notice: Subject to any disclaimer, the term of this patent is extended or adjusted under 35 U.S.C. 154(b) by 441 days.

(21) Appl. No.: 10/236,362

(22) Filed: Sep. 6, 2002

(65) Prior Publication Data
US 2004/0047931 A1    Mar. 11, 2004

(51) Int. Cl.
*A61K 38/43* (2006.01)
*A61K 31/19* (2006.01)
*A61K 35/78* (2006.01)

(52) U.S. Cl. .................. 424/78.03; 424/62; 424/74; 424/401; 424/725; 424/757; 424/770

(58) Field of Classification Search .................. 424/62, 424/78.03, 725, 757, 401, 770, 74
See application file for complete search history.

(56) References Cited

U.S. PATENT DOCUMENTS

| | | | |
|---|---|---|---|
| 4,771,060 A | 9/1988 | Nakagawa et al. | 514/365 |
| 4,919,921 A | 4/1990 | Hatae | 424/62 |
| 4,990,330 A | 2/1991 | Oyama | 424/59 |
| 5,145,781 A | 9/1992 | Suzuki et al. | 435/99 |
| 5,232,769 A | 8/1993 | Yamato et al. | 428/240 |
| 5,262,153 A | 11/1993 | Mishima et al. | 424/62 |
| 5,523,077 A | 6/1996 | Pawelek et al. | 424/62 |
| 5,609,875 A | 3/1997 | Hadas | 424/195.1 |
| 5,747,006 A | 5/1998 | Dornoff et al. | 424/62 |
| 5,824,327 A | 10/1998 | Whittemore et al. | 424/401 |
| 5,916,915 A | 6/1999 | Hong et al. | 514/474 |
| 5,980,904 A | 11/1999 | Leverett et al. | 424/195.1 |
| 5,993,835 A | 11/1999 | Mishima | 424/401 |
| 6,007,823 A | 12/1999 | Abbott et al. | 424/195.1 |
| 6,077,503 A | 6/2000 | Dornoff | 435/62 |
| 6,083,976 A | 7/2000 | Padmapriya et al. | 514/456 |
| 6,251,877 B1 | 6/2001 | Park et al. | 514/54 |
| 6,365,137 B1 | 4/2002 | Aust et al. | 424/62 |
| 6,417,226 B1 | 7/2002 | Perricone | 514/474 |
| 6,649,177 B1* | 11/2003 | Howard et al. | 424/401 |
| 6,716,599 B1* | 4/2004 | Howard et al. | 435/68.1 |
| 6,890,566 B1* | 5/2005 | Arquette | 424/725 |
| 2003/0023040 A1* | 1/2003 | Howard et al. | 530/377 |
| 2003/0044477 A1 | 3/2003 | Tang et al. | 424/757 |
| 2004/0047931 A1* | 3/2004 | Arquette | 424/770 |
| 2004/0052740 A1* | 3/2004 | Arquette | 424/62 |
| 2004/0137091 A1* | 7/2004 | Bassi et al. | 424/757 |
| 2004/0191335 A1* | 9/2004 | Bassi et al. | 424/757 |

OTHER PUBLICATIONS

Toshiyuki Suzuki, "Whitening Cosmetics", pp. 23-34.
Jaime Wisniak, "The Chemistry and Technology of Jojoba Oil", pp. 1-272.

* cited by examiner

Primary Examiner—Herbert J. Lilling
(74) Attorney, Agent, or Firm—Dale F. Regelman (57) ABSTRACT A composition which is effective as a skin whitening agent is disclosed. The composition includes Simmondsin. In certain embodiments, the composition comprises an extract of jojoba. A method of promoting skin whitening, comprising the step of topically administering to an individual a composition in an amount effective to whiten skin, where that composition comprises a jojoba extract.

10 Claims, 5 Drawing Sheets

COMPOSITION AND METHOD TO WHITEN SKIN

FIELD OF THE INVENTION

Applicant's invention relates to a composition and method to whiten skin.

BACKGROUND OF THE INVENTION

Exposure to the sun over time can induce many biochemical reactions in the skin. For example, exposure can lead to sunburn and tanning, which are immediate and well recognized. Other consequences of exposure to the sun are more subtle and accumulate over time. Often melanocytes can accumulate and the action of the enzyme tyrosinase is increased. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an even-looking skin tone and a more youthful appearance, is highly desired in today's society. Many people desire to modify their skin tone, to reduce aging spots, melasma, etc., or for purely cosmetic reasons. In fact, in the Far East, a lighter skin tone is desirable and is associated with higher socio-economic status.

Hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase.

It is desirable to realize a way of formulating a composition which can be effectively used as a topically applied skin whitening agent. In particular, identifying a composition that has improved stability and efficacy relative to those described in the prior art would be of significant commercial interest. Applicant has now discovered a composition comprising tyrosinase inhibitors, and/or melanin cell synthesis inhibitors, which is useful in topically applied cosmetic and pharmaceutical formulations.

SUMMARY OF THE INVENTION

Applicants' invention includes a composition which is effective as a skin whitening agent. Applicant's composition includes Simmondsin. In certain embodiments, Applicant's composition comprises an extract of jojoba. By "jojoba," Applicant means any portion of the jojoba plant, including without limitation jojoba seed. Applicant's invention further includes a method of promoting skin whitening, comprising the step of topically administering to an individual a composition in an amount effective to whiten skin, where that composition comprises a jojoba extract.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Referring to the illustrations, like numerals correspond to like parts depicted in the figures. The invention will be described as embodied in a Formulation A having a first molecular weight distribution of amino acids and peptide fragments and a Formulation B having a second molecular weight distribution of amino acids and peptide fragments. By "peptide fragments" and "protein fragments", Applicant means one or more amino acid oligomers/polymers produced by cleaving one or more amide bonds in one or more proteins produced by the jojoba plant.

Applicant's invention, however, is not limited to these embodiments. Rather, Applicant's invention includes a composition derived from jojoba using multiple extractions with different solvents, optionally followed by cleavage of one or more peptide linkages in a plurality of jojoba-derived proteins. Applicant's invention further includes a method for forming Applicant's composition. Applicant's invention further includes use of Applicant's composition to affect the visual appearance of skin.

All patents, applications, test methods and publications referenced in this specification are hereby incorporated by reference in their entirety. In case of conflict, the present description, including definitions, will prevail. The present invention is directed in part to compositions which is useful as a skin whitening agent that does not have the stability problems associated with whitening agents currently available. Specifically, the invention is directed in part to compositions comprising extracts of jojoba. Applicant's composition includes Simmondsin and/or Simmondsin derivatives. In certain embodiments, Applicant's composition further comprises a plurality of peptide fragments. By "peptide fragments," Applicant means one or more amino acid oligomers derived from the cleavage of one or more jojoba proteins. In certain embodiments, Applicant's composition further includes a plurality of amino acids. Such amino acids comprise naturally-occurring amino acids, non-naturally-occurring amino acids, and mixtures thereof.

Figure 1:
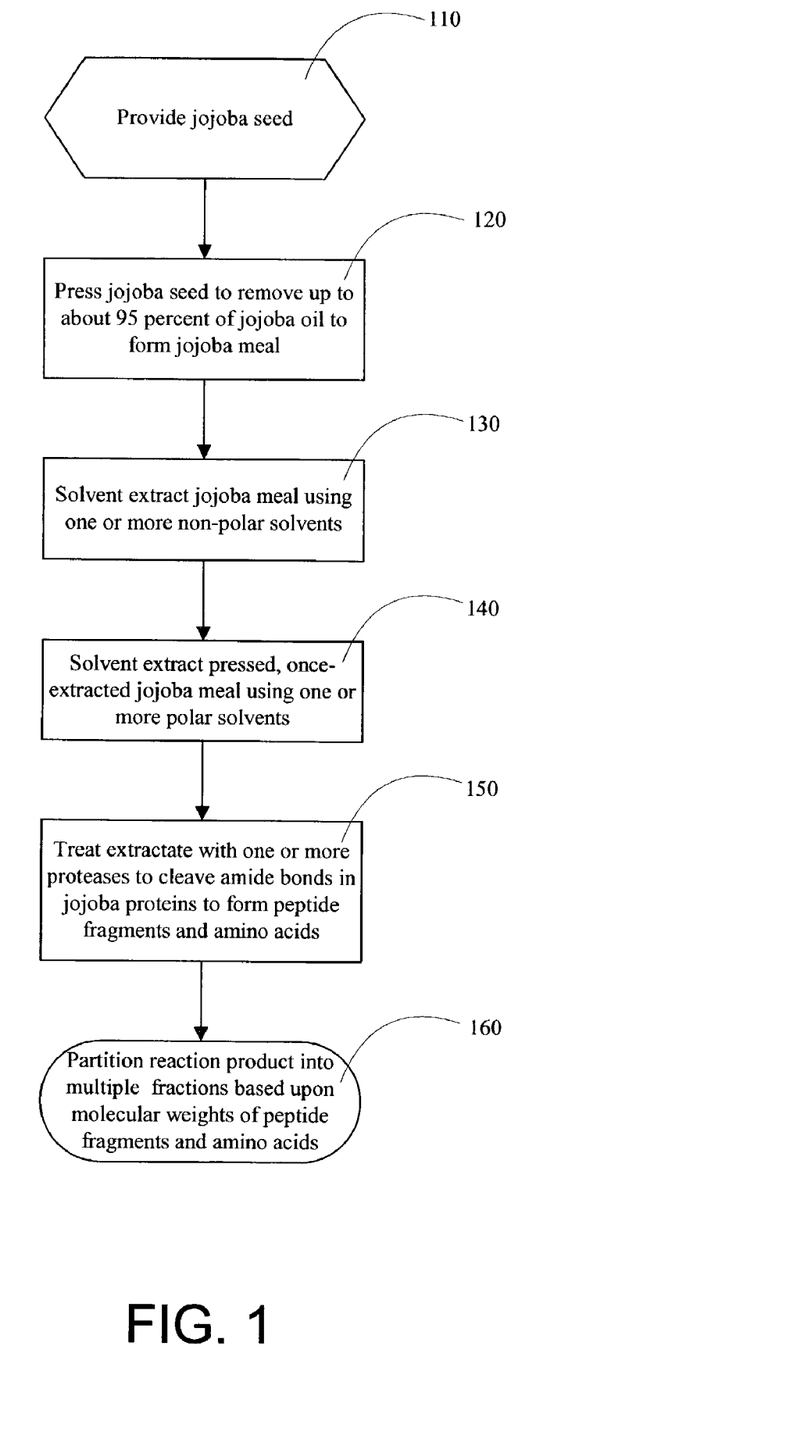
FIG. 1 is a flow chart summarizing the steps of Applicant's method to form his composition.

FIG. 1 summarizes Applicant's method to prepare his composition. Referring now to FIG. 1, in step 110 one or more parts of the jojoba plant are provided. Such jojoba plant parts include, without limitation, seed, hulls, bark, roots, leaves, stems, and the like. In certain embodiments, step 110 includes providing jojoba seed. In certain embodiments, jojoba seed is provided by the Desert Whale Jojoba Company of Tucson, Ariz. Jojoba seed comprises approximately 50 percent jojoba oil. The various parts of the jojoba plant, including jojoba seed, further comprises a complex mixture of jojoba oil, jojoba proteins, carbohydrates, Simmondsin, Simmondsin derivatives, and other phytochemicals.

In step 120, Applicant presses jojoba plant parts of step 110 to remove about 90 percent of the jojoba oil. In certain embodiments, such mechanical pressing is performed using an expeller apparatus. The solid material remaining after removal of jojoba oil from jojoba plant parts is sometimes referred to as "jojoba meal." This jojoba meal comprises up to about 12 percent residual jojoba oil in addition to a complex mixture of jojoba proteins, sugars, Simmondsin, and other phytochemicals.

In step 130, the jojoba meal of step 120 is extracted using one or more non-polar compounds. By a non-polar compound, Applicant means a material having a dielectric constant of about 2 or less. Such non-polar compounds include, without limitation, pentane, hexane, cyclohexane, and the like.

Applicant has discovered that in order to extract the jojoba-derived compounds having skin whitening effect, the jojoba meal must be milled to a powder. In certain embodiments, the milled jojoba meal has a average particle size of 50 microns with a standard deviation of 1.83. In certain embodiments, the milled jojoba meal has no particles larger than about 180 microns. In certain embodiments, step 130 includes milling the jojoba meal to a powder.

Prior art methods to extract jojoba meal use the meal in its "as-pressed" condition after removal of jojoba oil from one or more jojoba plant parts. Such prior art jojoba meal comprises particles larger than about 2,000 microns. Further processing of such macroscopic jojoba meal particles does not provide a composition having maximal skin whitening properties.

In certain embodiments, step 130 further includes using super critical $CO_2$ to extract the jojoba meal. Super critical carbon dioxide comprises highly pressurized carbon dioxide. At pressures of 250 to 350 times atmospheric pressure, $CO_2$ takes on the density of a liquid and the viscosity of a gas, making it an efficient solvent. In its pressurized state, $CO_2$ is pumped into a sealed chamber containing jojoba meal, where it is allowed to circulate to remove the residual jojoba oil. Two of the major advantages of $CO_2$ are that it does not leave a chemical residue and it has a minimal to no effect on the structure of the extracted jojoba oil.

In certain embodiments, step 130 includes extracting the pressed jojoba plant parts with one or more solvents having a dielectric constant of about 6 or less. Such solvents include, without limitation, methyl formate, methyl acetate, ethyl acetate, ethers, and halogenated alkyls.

In step 140, the non-polar solvent extracted jojoba meal is extracted with one or more polar compounds. By polar compound, Applicant means a material having a dielectric constant of about 10 or more. Such compounds include, without limitation, water, organic acids, inorganic acids, organic bases, inorganic bases, linear and cyclic alcohols, linear and cyclic ketones, dimethylsulfoxide, dimethylsulfone, and the like. In certain embodiments, step 140 further includes milling the jojoba meal to a powder.

In certain embodiments, Applicant's method transitions from step 140 to step 150. In certain embodiments, Applicant's method transitions from step 140 to step 160. In certain embodiments, Applicant's method transitions from step 140 to step 170. In certain embodiments, Applicant's method transitions from step 140 to step 195.

In step 150, the polar solvent extract of step 140 is treated with one or more compounds to effect cleavage of one or more amide bonds in one or more jojoba-derived proteins. In certain embodiments, step 150 includes using one or more protease enzymes. In certain embodiments, step 150 includes using one or more acids, such as hydrochloric acid.

In step 160, the extract of step 140 or the reaction mixture of step 150 is partitioned into multiple fractions, where each of those fractions comprises a different molecular weight distribution of amino acids, and/or peptide fragments, and/or jojoba proteins. In certain embodiments, the one or more fractions of step 160 further include one or more carbohydrate compounds. In certain embodiments, the one or more fractions of step 160 further include Simmondsin and/or Simmondsin derivatives. In certain embodiments, the one or more fractions of step 160 further include jojoba oil. Applicant's method transitions from step 160 to step 195.

In step 170, Applicant's method removes the one or more polar compounds from the extract of step 140 to form a material having up to 100 percent solids. Step 170 includes conventional methods and apparatus such as rotary evaporation, atmospheric evaporation, use of a fluidized bed, and the like. Applicant's method transitions from step 170 to step 180 wherein the high percentage solids material of step 170 is extracted with one or more alcoholic solvents. In certain embodiments, step 180 includes extracting the solids of step 170 with ethanol. In certain embodiments, Applicant's method transitions from step 180 to step 195.

In certain embodiments, Applicant's method transitions from step 180 to step 190 wherein the one or more alcohols of step 180 are removed to give a solid material. U.S. Pat. No. 6,007,823, in the name of Abbott et al., and incorporated by reference herein, describes methods to sequentially extract jojoba meal with hexane and water, concentrate the aqueous extract, extract that concentrate with ethanol, and concentrate that ethanolic extract to give a solid material comprising Simmondsin. Applicant's method transitions from step 190 to step 195.

In step 195, Applicant's method forms Applicant's skin whitening composition using the extract of step 140, and/or the one or more of the partitioned fractions of step 160, and/or the extract of step 180, and/or the solid material of step 190.

In certain embodiments, Applicant's composition, formed using steps 110, 120, 130, 140, 170, 180, optionally 190, and 195, is essentially free of proteins, peptide fragments, and amino acids. In certain embodiments, Applicant's composition, formed using steps 110, 120, 130, 140, and 195, includes up to about 25 weight percent of jojoba proteins. In certain embodiments, Applicant's composition, formed using steps 110, 120, 130, 140, 150, 160, and 195, includes up to about 25 weight percent of a plurality of amino acids an/or a plurality of peptide fragments.

Example I is presented to further illustrate to persons skilled in the art how to make and use the invention and to identify certain embodiments thereof. This example is not intended as a limitation, however, upon the scope of the invention, which is defined only by the appended claims.

EXAMPLE I

One thousand pounds of hexane-extracted jojoba meal having a residual jojoba oil concentration of about 1.7% was treated in 750 gallons of water at about 140° F. with 22 pounds of 50% NaOH solution for about 60 minutes. Thereafter, 15 pounds of a first protease enzyme, sold in commerce under the tradename ALCALASE by Novo, was added, and the mixture agitated for about 2 hours. The pH of the reaction mixture was maintained between about 7.5 and about 8.0 using 50% NaOH. An additional 15 pounds of ALCALASE was added, and agitation continued for about another 2 hours.

The pH was then adjusted to about 6.5 using lactic acid. Thereafter, 10 pounds of a second protease enzyme, sold in commerce under the tradename FLAVORZYME by Novo, was added, and the reaction mixture agitated for about 4 hours. Thereafter, 3 pounds of a third protease enzyme, sold in commerce under the tradename DUAL PROTEASE ENZYME by Enzyme Development Corp., was added, and the reaction mixture agitated for an additional 2 hours.

Lactic acid was then added to the reaction mixture to lower the pH to about 4.5. Thereafter, 8 pounds of sodium metabisulfite was added and the reaction mixture agitated for about 10 minutes. The reaction mixture was then heated to about 160° F. to deactivate the first protease enzyme, the second protease enzyme, and the third protease enzyme. The reaction mixture was then filtered using a rotary vacuum filter, and the filtrate was clarified by passage through a packed-house filter unit. The clarified filtrate was then separated into two fractions using a nanofiltration membrane system.

The retenate fraction, i.e. that fraction of the clarified filtrate that did not pass through the nanofiltration system, was chilled to about 34–35° F. and allowed to stand for about 16–24 hours. The chilled retenate fraction was then cold-filtered to remove haziness, aged 1–2 weeks, packaged, and used thereafter as Applicant's Formulation A. The permeate, i.e. the fraction passing through the filtration system, was evaporated to a solids content of about 34%, and then aged, filtered, packaged, and used thereafter as Applicant's Formulation B.

Formulation A and Formulation B were tested for residual protease activity. Azocasein, a protein, was subjected to digestion for 20 minutes at 50° C. with samples of either Formulation A or Formulation B. After digestion, the undigested portion of the protein was precipitated, filtered, and discarded. The supernatant was treated with alkali to develop color. The color of the supernatant was determined using a spectrophotometer at 440 nm wavelength. The Optical Density of the supernatant was zero indicating an absence of residual protease activity in Formulation A and in Formulation B.

Table I recites the weight percent of the amino acid portion of Formulations A and B. Table I includes data for a first sample of Formulation A, identified as Formulation $A_1$, and a second sample of Formulation A, identified as Formulation $A_2$. Table I further includes data for a first sample of Formulation B, identified as Formulation $B_1$, and a second sample of Formulation B, identified as Formulation $B_2$.

TABLE I

| FORMULATION | $B_1$ | $B_2$ | $A_1$ | $A_2$ |
| --- | --- | --- | --- | --- |
| Lysine | 0.03 | 0.05 | 0.26 | 0.34 |
| Histidine | 0.01 | 0.02 | 0.08 | 0.15 |
| Arginine | 0.05 | 0.08 | 0.43 | 0.51 |
| Aspartic Acid | 0.13 | 0.19 | 0.77 | 0.99 |
| Threonine | 0.06 | 0.08 | 0.34 | 0.43 |
| Serine | 0.08 | 0.12 | 0.33 | 0.42 |
| Glutamic Acid | 0.20 | 0.25 | 1.13 | 1.14 |
| Proline | 0.04 | 0.06 | 0.39 | 0.37 |
| Glycine | 0.10 | 0.12 | 0.46 | 0.50 |
| Alanine | 0.09 | 0.12 | 0.29 | 0.36 |
| Valine | 0.07 | 0.08 | 0.38 | 0.46 |
| Methionine | 0.02 | 0.02 | 0.08 | 0.10 |
| Isoleucine | 0.05 | 0.05 | 0.27 | 0.30 |
| Leucine | 0.09 | 0.10 | 0.45 | 0.51 |
| Tyrosine | 0.01 | 0.06 | 0.10 | 0.33 |
| Phenylalanine | 0.07 | 0.07 | 0.27 | 0.30 |
| Cystine | 0.01 | 0.02 | 0.10 | 0.15 |
| Tryptophan | 0.01 | 0.01 | 0.01 | 0.05 |

In certain embodiments, Formulation A comprises between about 5 weight percent amino acids and peptide fragments to about 10 weight percent amino acids and peptide fragments. In certain embodiments, Formulation A comprises about 7.41 weight percent amino acids and peptide fragments. In certain embodiments, Formulation A comprises a mixture of peptide fragments having weight average molecular weights between about 1,000 Daltons and about 5,000 Daltons. In certain embodiments, Formulation A comprises a mixture of peptide fragments having an average molecular weight of about 3,500 Daltons.

As those skilled in the art will appreciate, a protease enzyme cleaves one or more amide linkages in a polypeptide chain, i.e. a protein, to give two smaller peptide fragments. Certain protease enzymes are amide bond specific, meaning that only an amide bond formed by two specific amino acids will be cleaved. By varying the number of protease enzymes used, and by varying the specificity of those protease enzymes, and by varying the reaction times using those protease enzymes, the molecular weight distribution of the peptide fragments of Formulation A can be changed. In certain embodiments, Formulation A comprises a mixture of peptide fragments having a weight average molecular weight range of between about 1,000 Daltons and about 10,000 Daltons. In certain embodiments, Formulation A comprises a mixture of peptide fragments having a weight average molecular weight range of between about 5,000 Daltons and about 10,000 Daltons. In certain embodiments, Formulation A comprises a mixture of peptide fragments having weight average molecular weights greater than about 10,000 Daltons.

In certain embodiments, Formulation B comprises between about 0.5 weight percent amino acids/peptide fragments and about 5 weight percent amino acids/peptide fragments. In certain embodiments, Formulation B comprises a mixture of amino acids and peptide fragments having molecular weights between about 75 and about 1,000. In certain embodiments, Formulation B comprises a mixture of amino acids and peptide fragments having an average molecular weight of about 200. By varying the number of protease enzymes used, and by varying the specificity of those protease enzymes, and by varying the reaction times using those protease enzymes, the molecular weight distribution of the amino acids and peptide fragments of Formulation B can be changed.

Applicant's composition includes Simmondsin and/or a mixture of Simmondsin derivatives. In certain embodiments, Applicant's composition comprises between about 0.01 weight percent and about 50 weight percent Simmondsin and/or a mixture of Simmondsin derivatives. Formulations A and B include Simmondsin and/or a mixture of Simmondsin derivatives. By Simmondsin, Applicant means Compound I wherein R2 is hydrogen, R3 is OH, R4 is $OCH_3$ and R5 is $OCH_3$. By Simmondsin derivative, Applicant means Compound I wherein R2 is other than hydrogen, R3 is other than OH, R4 is other than $OCH_3$, and R5 is other than $OCH_3$.

In certain embodiments, the R2 moiety of Compound I comprises a Ferulic acid moiety comprising compound II.

Table 2 summarizes certain embodiments of Simmondsin and/or Simmondsin derivatives that are found in Applicant's composition, including the embodiments of Formulation A and Formulation B.

TABLE 2

| Compound | R2 | R3 | R4 | R5 | Name |
|---|---|---|---|---|---|
| III | H | OH | OCH$_3$ | OCH$_3$ | Simmondsin |
| IV | H | OH | OH | OCH$_3$ | 4-Demethylsimmondsin |
| V | H | OH | OCH$_3$ | H | 5-Demethylsimmondsin |
| VI | H | OH | OH | OH | Didemethylsimmondsin |
| VII | Compound II | OH | OCH$_3$ | OCH$_3$ | Simmondsin 2'-trans-ferulate |
| VIII | OH | Compound II | OCH$_3$ | OCH$_3$ | Simmondsin 3'-trans-ferulate |
| IX | Compound II | OH | OH | OCH$_3$ | 4-Demethylsimmondsin 2'-trans-ferulate |
| X | Compound II | OH | OCH$_3$ | OH | 5-Demethylsimmondsin 2'-trans-ferulate |
| XI | Compound II | OH | OH | OH | Didemethylsimmondsin trans-ferulate |

Applicant's Formulation A includes Simmondsin/Simmondsin derivatives at a weight percent between about 1 weight percent and about 5 weight percent. In certain embodiments, Formulation A comprises about 2.36 weight percent Simmondsin/Simmondsin derivatives. Applicants' Formulation B includes Simmondsin/Simmondsin derivatives at a weight percentage between about 0.1 weight percent and about 2.5 weight percent. In certain embodiments, Formulation A comprises about 0.44 weight percent Simmondsin/Simmondsin derivatives.

In certain embodiments, Applicant's composition, including the embodiments of Formulations A and B, comprises jojoba oil. In certain embodiments, the jojoba oil component comprises part or all of the residual jojoba oil in the starting pressed, once-extracted, jojoba meal. In other embodiments, additional jojoba oil is added to Applicant's composition, including the embodiments of Formulations A and B. Jojoba oil is obtained from the seed of the shrub Simmondsiachinensis which is native to the Sonoran desert. Jojoba oil is a mixture of naturally-occurring compounds obtained from the jojoba seed, sometimes called the jojoba bean. Jojoba seed contains about 50 weight percent of a yellow oil commonly referred to as jojoba oil. In contrast to other vegetable oils which comprise a mixture of triglycerides, jojoba oil comprises a mixture of long-chain esters.

As those skilled in the art will appreciate, carboxylic ester XV can be formed by the reaction of alcohol XIV and carboxylic acid XIII. In addition, an ester-group-containing compound, such as many of the constituents of jojoba oil, can be described as comprising an R5 component and an R6 component.

Jojoba oil includes a variety of ester-group-containing compounds wherein the R7 component comprises a mixture of carbon-containing moieties having, primarily, 17, 18, 20, and 22 carbon atoms, and wherein the R6 component comprises a mixture of carbon-containing moieties having, primarily, 19, 20, 22, and 24 carbon atoms. Furthermore, it is known that the R7 component of these various jojoba oil ester-group-containing constituents includes at least one carbon-carbon double bond having a cis-configuration. Sometimes such a cis-configuration is known as the Z-configuration. It is further known that the R6 component of these various jojoba oil ester-group-containing constituents includes at least one carbon-carbon double bond having a cis-configuration. Sometimes such a cis-configuration is known as the Z-configuration.

By "jojoba oil," Applicant means naturally-occurring jojoba oil and/or one or more derivatives of naturally-occurring jojoba oil. Certain derivatives of jojoba oil are known in the art. For example, isomerization of the double bond in the R7 component, and/or the R6 component, of the various jojoba esters from the cis configuration to a trans configuration yields a material that is solid at room temperature, where that solid material includes one or more crystalline compounds. U.S. Pat. No. 4,329,298 teaches a method to isomerize jojoba oil and is hereby incorporated herein by reference.

In addition, hydrogenation of the double bond in the R7 component, and/or hydrogenation of the double bond in the R6 component, of the jojoba oil ester yields a crystalline, wax-like material. Substantially fully hydrogenated jojoba oil is a solid with a melting point upwards of 70° C. As those skilled in the art will appreciate, the degree of hydrogenation can be measured using an Iodine Value ("IV"). Naturally-occurring jojoba oil has an IV of between about 80 and 85. As the percentage of carbon-carbon double bonds hydrogenated increases, the IV of that hydrogenated material decreases. As the percentage of carbon-carbon double bonds hydrogenated increases, the degree of crystallinity and the melting point of that hydrogenated material also increase.

In certain embodiments, Applicant's composition, including the embodiments of Formulations A and B, comprises between about 0.05 weight percent and about 90 weight percent jojoba oil. By jojoba oil, Applicant means a naturally-occurring mixture of ester compounds obtain from jojoba seed, isomerized jojoba oil, partially or fully hydrogenated jojoba oil, and mixtures thereof.

In certain embodiments, Applicant's composition, including the embodiments of Formulations A and B, further comprises a plurality of carbohydrate compounds. In certain embodiments, Applicant's composition comprises one or more monosaccharides, one or more disaccharides, and one or more complex saccharides.

In certain embodiments, Applicant's composition comprises fructose. In certain embodiments, for example, Formulation A comprises fructose in a weight percentage of between about 0.50 and about 5.0. In certain embodiments, Formulation A comprises fructose in a weight percentage of about 2.41. In certain embodiments, Formulation B comprises fructose in a weight percentage of between about 0.25 and about 2.5. In certain embodiments, Formulation B comprises fructose in a weight percentage of about 1.13.

In certain embodiments, Applicant's composition comprises glucose. In certain embodiments, for example, Formulation A comprises glucose in a weight percentage of between about 0.25 and about 2.5. In certain embodiments, Formulation A comprises glucose in a weight percentage of about 1.32. In certain embodiments, Formulation B comprises glucose in a weight percentage of between about 0.25 and about 2.5. In certain embodiments, Formulation B comprises glucose in a weight percentage of about 1.42.

In certain embodiments, Applicant's composition comprises sucrose. In certain embodiments, for example, Formulation A comprises sucrose in a weight percentage of between about 0.10 and about 1.0. In certain embodiments, Formulation A comprises sucrose in a weight percentage of about 0.57. In certain embodiments, Formulation B comprises sucrose in a weight percentage of between about 0.05 and about 0.50. In certain embodiments, Formulation B comprises sucrose in a weight percentage of about 0.13.

In certain embodiments, Applicant's composition comprises raffinose, i.e. a trisaccharide. In certain embodiments, for example, Formulation A comprises raffinose in a weight percentage of between about 0.05 and about 0.50. In certain embodiments, Formulation A comprises raffinose in a weight percentage of about 0.26.

Examples II, III, and IV, are presented to further illustrate to persons skilled in the art how to make and use the invention and to identify certain embodiments thereof. These examples are not intended as limitations, however, upon the scope of the invention, which is defined only by the appended claims.

Table 3 recites information generated in testing the tyrosinase activity inhibition shown by Formulation A and Formulation B. Test solutions using mouse melanoma cells B16F10 were prepared, and 50 micromoles of Formulation A or Formulation B, along with L-DOPA at 0.025%, were added to those test solutions. The test solutions were incubated from about 1 hour to about 3 hours. The melanin content of the test solutions were measured before and after incubation using photo absorption methods. The tyrosinase activities were determined using those melanin values.

TABLE 3

| Concentration, v/v % | Tyrosinase Activity (%) measured using Formulation A | Tyrosinase Activity (%) measured using Formulation B |
|---|---|---|
| 0 | 100 | 110 |
| 0.02 | 97 | 104.3 |
| 0.05 | 95.2 | 103.7 |
| 0.1 | 89.1 | 105.2 |

TABLE 3-continued

| Concentration, v/v % | Tyrosinase Activity (%) measured using Formulation A | Tyrosinase Activity (%) measured using Formulation B |
|---|---|---|
| 0.3 | 77.1 | 102.6 |
| 0.6 | 56 | 98.3 |
| 1.2 | 10.4 | 78.3 |
| 2.5 | −3.1 | 52.7 |

Figure 2:
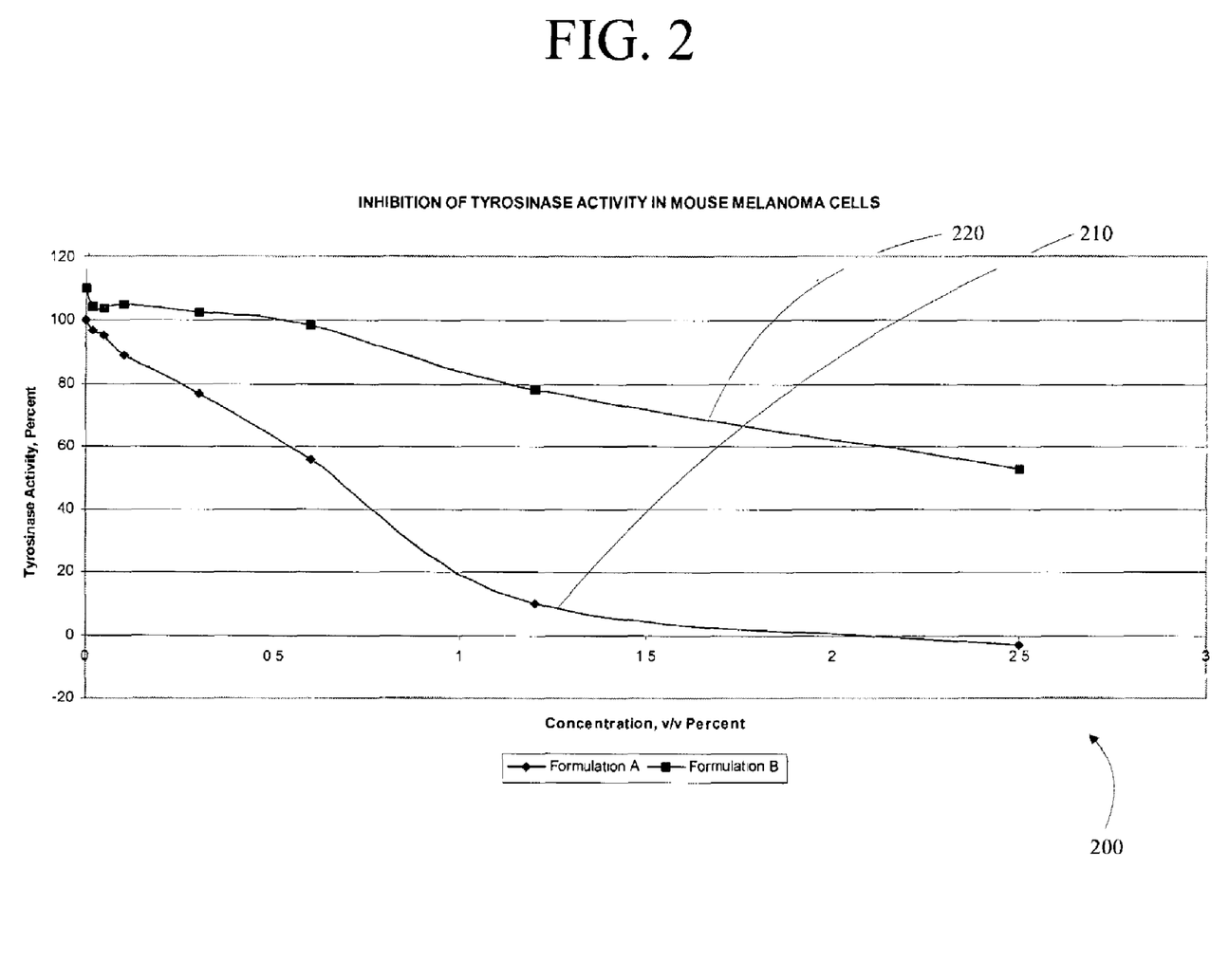
FIG. 2 is a graph showing the tyrosinase activity inhibition in mouse melanoma cells observed using two embodiments of Applicant's composition.

FIG. 2 graphically depicts the data of Table 2. Referring now to FIG. 2, graph 200 includes curve 210 and curve 220. Curve 210 shows the tyrosinase activity as a function of the concentration of Formulation A. As curve 210 shows, Formulation A clearly exhibits a dose-dependent tyrosinase activity inhibition. Therefore, topical application of Formulation A will cause a skin whitening effect. Curve 220 shows the tyrosinase activity as a function of the concentration of Formulation B. As curve 220 shows, Formulation B clearly exhibits a dose-dependent tyrosinase activity inhibition. Therefore, topical application of Formulation B will cause a skin whitening effect.

EXAMPLE III

Table 4 recites information generated in testing the tyrosinase activity inhibition shown by Formulation A and Formulation B. Test solutions using human melanocyte cells NHEM were prepared, and 50 micromoles of Formulation A or Formulation B, along with L-DOPA at 0.025%, were added to those test solutions. The test solutions were incubated from about 1 hour to about 3 hours. The tyrosinase activities of the test solutions were measured before and after incubation using photo absorption methods.

TABLE 4

| Concentration, v/v % | Tyrosinase Activity (%) measured using Formulation A | Tyrosinase Activity (%) measured using Formulation B |
|---|---|---|
| 0 | 100 | 100 |
| 0.02 | 99 | 101.2 |
| 0.05 | 94.6 | 98.3 |
| 0.1 | 92.7 | 97.8 |
| 0.3 | 78.6 | 91.8 |
| 0.6 | 56.7 | 85.7 |
| 1.2 | 39.2 | 69.4 |
| 2.5 | 1.2 | 29.5 |

Figure 3:
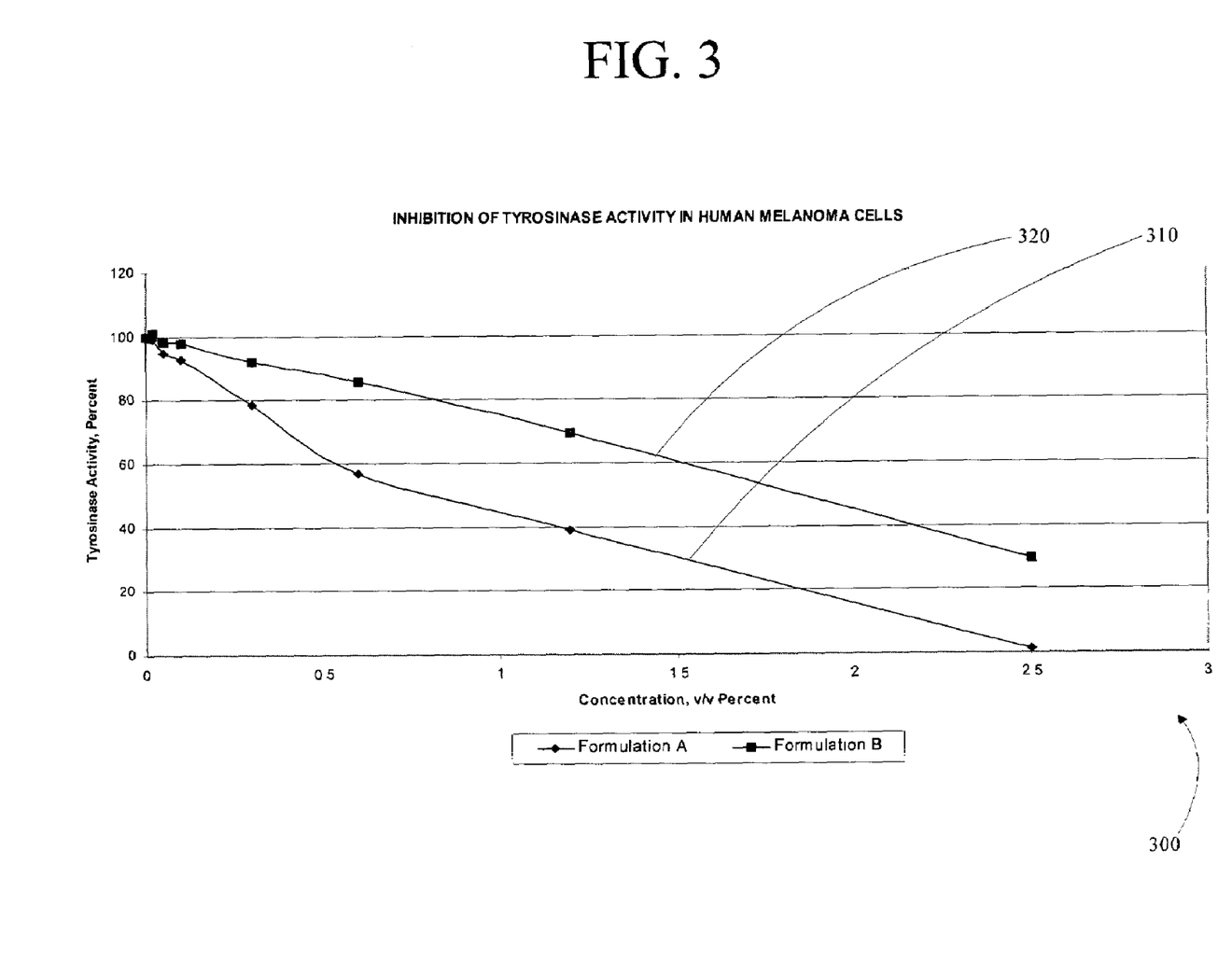
FIG. 3 is a graph showing the tyrosinase activity inhibition in human melanoma cells observed using two embodiments of Applicant's composition.

FIG. 3 graphically depicts the data of Table 4. Referring now to FIG. 3, graph 300 includes curve 310 and curve 320. Curve 310 shows the tyrosinase activity as a function of the concentration of Formulation A. As curve 310 shows, Formulation A clearly exhibits a dose-dependant tyrosinase activity inhibition. Therefore, topical application of Formulation A will cause a skin whitening effect. Curve 320 shows the tyrosinase activity as a function of the concentration of Formulation B. Formulation B clearly exhibits a dose-dependent tyrosinase activity inhibition. Therefore, topical application of Formulation B will cause a skin whitening effect.

EXAMPLE IV

Table 5 recites data relating to the melanin content of mouse B16F10 melanoma cells in the presence of various concentrations of Formulation A and various concentrations of Formulation B. Mouse B16F10 melanoma cells were prepared on a plate with about 2,000 cells in Dulbecco's Modified Eagle Medium with 5% v/v Fetal Bovine Serum. Those cells were cultured. A specific concentration of either Formulation A or Formulation B was added, and the test sample cultured for 6 days. Thereafter, the cells were washed out off the plates with Phosphate Buffer Saline Solution, and cell pellets were prepared. The color of each cell pellet was determined, and classified between 5 (black) to 1 (white) with 0 meaning not detectable. The protein content of each cell pellet was then determined, and the total melanin content in micrograms was calculated per microgram of protein. A Negative Control experiment was performed wherein no skin whitening agent was added to the cells. Positive Control experiments were performed wherein Sodium lactate was added to test cultures at either a 25 mM level or a 50 mM level.

TABLE 5

| Concentration v/v % | Negative Control | Positive Control | Formulation A | Formulation B |
|---|---|---|---|---|
| 0.2 | 0.543 |  | 0.169 | 0.344 |
| 0.5 | 0.543 | 0.240 | 0.194 | 0.322 |
| 1.0 | 0.543 | 0.107 | 0.187 | 0.213 |

Figure 4:
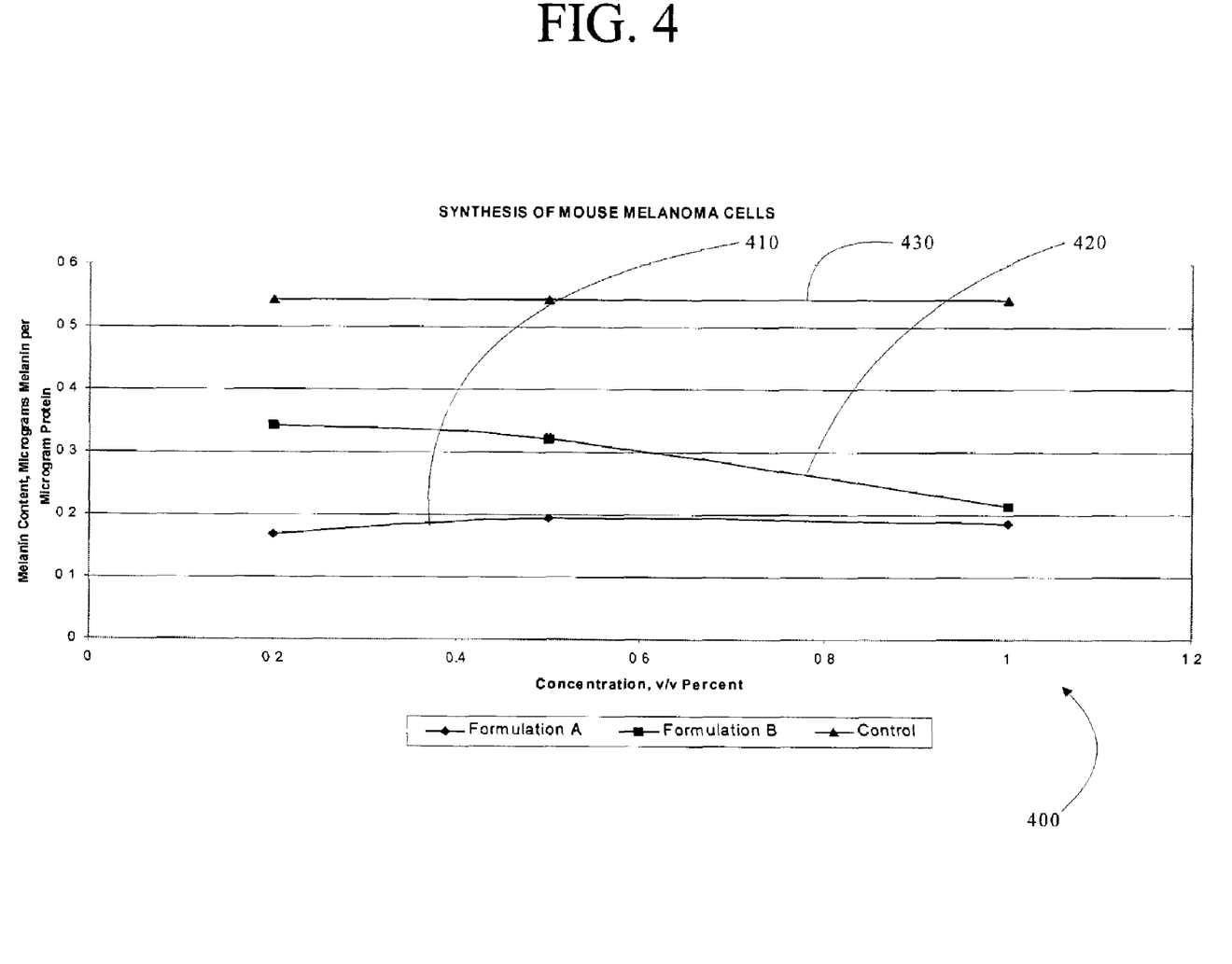
FIG. 4 is a graph showing the melanin synthesis inhibition in mouse melanoma cells observed using two embodiments of Applicant's composition.

FIG. 4 graphically depicts the data of Table 5. Referring now to FIG. 4, graph 400 includes curve 410, curve 420, and curve 430. Curve 430 shows the melanin content in micrograms per microgram of protein for the negative control experiment. Curve 410 shows the melanin content as a function of the concentration of Formulation A. As curve 410 shows, Formulation A clearly causes a melanin cell synthesis inhibition. Therefore, topical application of Formulation A will cause skin whitening. As curve 420 shows, Formulation B clearly causes a melanin cell synthesis inhibition. Therefore, topical application of Formulation B will cause skin whitening.

Table 6 recites the observed Vidjual color determinations for the cell pellets. A Vidjual score of 5 means the cell pellet was black. A Vidjual score of 1 means the cell pellet was white. A Vidjual score of 0 means the cell pellet was not detectable, i.e. it has no color at all.

TABLE 6

| Concentration v/v % | Negative Control | Positive Control | Formulation A | Formulation B |
|---|---|---|---|---|
| 0.2 | 5 |  | 3 | 4 |
| 0.5 | 5 | 3 | 3 | 4 |
| 1.0 | 5 | 1 | 0 | 0 |

Figure 5:
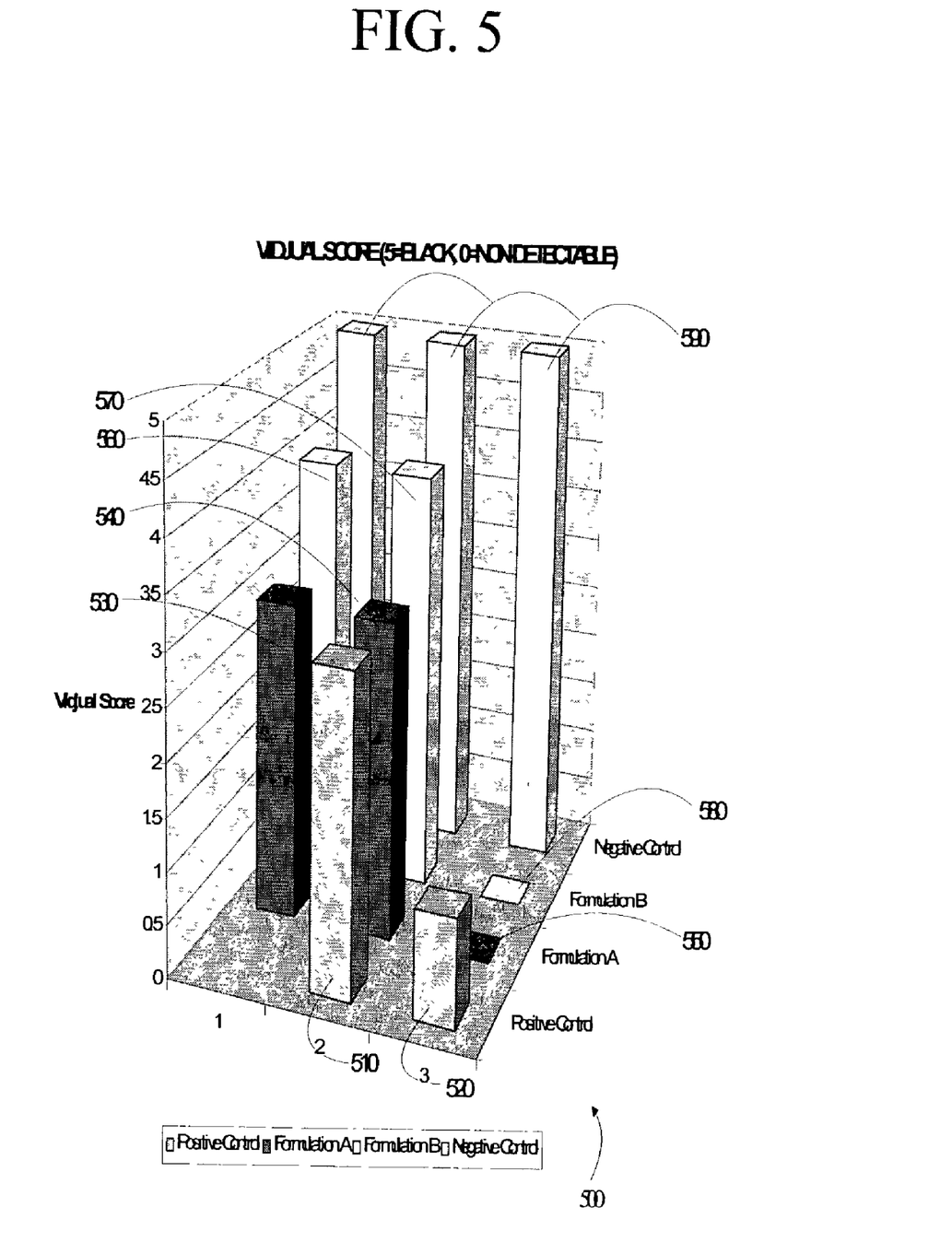
FIG. 5 is a chart showing the whitening effect in mouse melanoma cells observed using two embodiments of Applicant's composition.

FIG. 5 graphically depicts the data of Table 6. Referring now to FIG. 5, graph 500 is a bar graph showing the observed Vidjual scores. Bars 590 show the high score, i.e. the black color, observed with the negative control. Bars 510 and 520 show the dose-dependent whitening effect of the sodium lactate positive control. Bars 530 and 540 show Vidjual scores of 3 for the lower concentrations of Formulation A. Bar 550 shows the dramatic whitening effect of Formulation A at a concentration of 1.0 v/v%. Bars 530, 540, and 550, demonstrate the tissue whitening effects of Formulation A.

Bars 560 and 570 show the Vidjual scores of 4 for the lower concentrations of Formulation B. Bar 580 shows the dramatic whitening effect of Formulation B at a concentration of 1.0 v/v %. Bars 560, 570, and 580, demonstrate the tissue whitening effects of Formulation A.

Formulation A and Formulation B were tested for in vitro dermal irritancy potential using an observed ET-50 test wherein normal, human-derived epidermal keratinocytes were treated with either 100% Formulation A, or with 100% Formulation B. Test cells were treated with Formulation A/Formulation B for about 1 hour to about 20 hours. The percentage of viable cells was then determined for each test sample using a spectrophotometric analysis at 570 nm. Thereafter, a semi-log plot of the percent viabilities, on the linear Y axis, versus the dosing times, on the log X axis. By interpolation, the time which the percent viability would equal 50%, i.e. the ET-50 time, was determined. A Sodium Lauryl Sulfate control showed an ET-50 time of less than 1 hour. A Triton X control elicited an ET-50 of 3.7 hours.

Formulation A showed an ET-50 time of 15.2 hours. Formulation A is categorized in the very mildly irritating range. Formulation B showed an ET-50 time of 9.3 hours. Formulation B is categorized in the mildly irritating range.

Formulation A and Formulation B were tested for in vitro EpiOcular irritancy potential using an observed ET-50 test wherein normal, human-derived epidermal keratinocytes which have been cultured to form a stratified, squamous epithelium similar to that found in cornea were treated with either 100% Formulation A, or with 100% Formulation B. Test cells were treated with Formulation A/Formulation B for about 5 minutes to about 4 hours. The percentage of viable cells was then determined for each test sample using spectrophotometric analysis at 570 nm. Thereafter, a semi-log plot of the percent viabilities, on the linear Y axis, versus the dosing times, on the log X axis. By interpolation, the time which the percent viability would equal 50%, i.e. the ET-50 time, was determined. Equation 1 can be used to estimate the rabbit Draize eye score:

$$DRAIZE = -4.74 + 101.7/(ET\text{-}50)^{1/2} \qquad (1)$$

Formulation A showed an ET-50 time greater than 256 minutes. Formulation A is categorized in the non-irritating classification. Formulation B showed an ET-50 time greater than 256 minutes. Formulation B is categorized in the non-irritating classification.

Formulation A and Formulation B were tested by repetitive epidermal contact to evaluate the potential to induce primary or cumulative irritation and/or allergic contact sensitization. Sixty (60) subjects, male and female, ranging in age from 17 to 77 years were selected. Fifty-Six (56) subjects completed the study. The study showed that Formulation A does not indicate a potential for dermal irritation or allergic contact sensitization. The study showed that Formulation B does not indicate a potential for dermal irritation or allergic contact sensitization.

In certain embodiments, Applicant's composition further includes a cosmetically acceptable carrier and/or a pharmaceutically acceptable carrier. By "cosmetically acceptable" and "pharmaceutically acceptable," Applicant means those drugs, medicaments, or inert ingredients which are suitable for use in contact with the tissues of humans and lower animals without undue toxicity, incompatibility, instability, irritation, and the like, commensurate with a reasonable benefit/risk ratio. In certain embodiments, the cosmetically acceptable vehicle will form from about 1 weight percent to about 99.9 weight percent of Applicant's composition. In certain embodiments, the cosmetically acceptable vehicle comprises between about 50 weight percent and about 99 weight percent of Applicant's composition. In certain embodiments, Applicant's composition comprises a cream, an ointment, a foam, a lotion, a plaster, or an emulsion.

One or more embodiments of Applicant's composition maybe included in a wide variety of personal care products. Such personal care products include, without limitation, skin exfoliation products, skin moisturizers, massage oils, soaps, sunscreens, skin cleaners, and the like.

The present invention contemplates a method of visibly whitening human skin comprising applying to the skin a composition containing a jojoba extract wherein the composition is applied in an amount and for a period of time sufficient to visibly whiten the skin. In certain embodiments, the composition is topically applied to darkened skin areas in a predetermined or as needed regimen either at intervals by application of a lotion or the like, it generally being the case that gradual lightening is noted with each successive application. Insofar as Applicant has determined, based upon in vitro testing, no adverse side effects will likely be encountered upon repetitive use of Applicant's composition.

While the preferred embodiments of the present invention have been illustrated in detail, it should be apparent that modifications and adaptations to those embodiments may occur to one skilled in the art without departing from the scope of the present invention as set forth in the following claims.

I claim:

1. A method of promoting skin whitening, comprising the step of topically administering to an individual a jojoba extract in an amount effective to whiten skin, wherein said jojoba extract is formed by the process of:
    providing jojoba meal;
    extracting said jojoba meal with a solvent having a dielectric constant of 10 or more;
    treating the jojoba extract with one or more protease enzymes.

2. The method of claim 1, further comprising repeating the topical administration of said composition as required for effectiveness.

3. A method to form a skin whitening composition, comprising the steps of:
    providing one or more jojoba plant parts;
    forming jojoba meal;
    milling said jojoba meal to a powder;
    extracting said milled jojoba meal with one or more compounds having a dielectric constant of about 10 or greater;
    filtering said extract to form said skin whitening composition;
    wherein said skin whitening composition inhibits melanin synthesis.

4. The method of claim 3, further comprising the step of:
    treating said jojoba meal with one or more compounds having a dielectric constant of about 6 or less prior to extraction of said jojoba meal with said one or more compounds having a dielectric constant of about 10 or greater.

5. The method of claim 4, wherein said one or more solvents having a dielectric constant of about 6 or less comprises super critical carbon dioxide.

6. The method of claim 4, further comprising the steps of treating said extract with one or more amide-cleaving compounds.

7. The method of claim 6, wherein said one or more amide cleaving compounds comprises a protease enzyme.

8. The method of claim 6, wherein said one or more amide cleaving compounds comprise two or more protease enzymes.

9. The method of claim 6, wherein said one or more amide cleaving compounds comprises an acid.

10. The method of claim 9, wherein said acid comprises hydrochloric acid.

* * * * *